(12) United States Patent
Craig

(10) Patent No.: US 8,235,987 B2
(45) Date of Patent: Aug. 7, 2012

(54) THERMAL PENETRATION AND ARC LENGTH CONTROLLABLE ELECTROSURGICAL PENCIL

(75) Inventor: Jason L. Craig, Loveland, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 601 days.

(21) Appl. No.: 12/275,290

(22) Filed: Nov. 21, 2008

(65) Prior Publication Data
US 2009/0149851 A1 Jun. 11, 2009

Related U.S. Application Data

(60) Provisional application No. 60/992,413, filed on Dec. 5, 2007.

(51) Int. Cl.
*A61B 18/18* (2006.01)

(52) U.S. Cl. .................. 606/41; 606/42; 606/45; 606/49

(58) Field of Classification Search .............. 606/41–52, 606/32, 34
See application file for complete search history.

(56) References Cited

U.S. PATENT DOCUMENTS

| | | | |
|---|---|---|---|
| 2,031,682 A | 2/1936 | Charles et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |

(Continued)

FOREIGN PATENT DOCUMENTS

DE 24 29 021 A1 1/1976

(Continued)

OTHER PUBLICATIONS

International Search Report from PCT-US03-37111; Jul. 21, 2004.

(Continued)

*Primary Examiner* — Matthew F Desanto

(57) ABSTRACT

An electrosurgical pencil is provided, which includes an elongated housing, an electrocautery electrode supported within the housing and extending distally from the housing. The electrocautery electrode is connected to a source of electrosurgical energy. The pencil also includes at least one voltage divider network supported on the housing and electrically connected to the source of electrosurgical energy for controlling intensity, frequency, and/or mode of electrosurgical energy being delivered to the electrocautery electrode.

27 Claims, 9 Drawing Sheets

U.S. PATENT DOCUMENTS

| | | |
|---|---|---|
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A | 7/1991 | Rydell |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,366,464 A | 11/1994 | Belknap |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |
| 5,531,722 A | 7/1996 | Van Hale |
| 5,549,604 A | 8/1996 | Sutcu et al. |
| 5,561,278 A | 10/1996 | Rutten |
| 5,601,224 A | 2/1997 | Bishop et al. |
| 5,609,573 A | 3/1997 | Sandock |
| 5,626,575 A | 5/1997 | Crenner |
| 5,630,417 A | 5/1997 | Petersen et al. |
| 5,630,426 A | 5/1997 | Eggers et al. |
| 5,630,812 A | 5/1997 | Ellman et al. |
| 5,633,578 A | 5/1997 | Eggers et al. |
| 5,634,912 A | 6/1997 | Injev |
| 5,634,935 A | 6/1997 | Taheri |

| Patent No. | Kind | Date | Inventor |
|---|---|---|---|
| 5,643,256 | A | 7/1997 | Urueta |
| D384,148 | S | 9/1997 | Monson |
| 5,669,907 | A | 9/1997 | Platt, Jr. et al. |
| 5,674,219 | A | 10/1997 | Monson et al. |
| 5,693,044 | A | 12/1997 | Cosmescu |
| 5,693,050 | A | 12/1997 | Speiser |
| 5,693,052 | A | 12/1997 | Weaver |
| 5,697,926 | A | 12/1997 | Weaver |
| 5,702,360 | A | 12/1997 | Dieras et al. |
| 5,702,387 | A | 12/1997 | Arts et al. |
| 5,712,543 | A | 1/1998 | Sjostrom |
| 5,713,895 | A | 2/1998 | Lontine et al. |
| 5,720,745 | A | 2/1998 | Farin et al. |
| D393,067 | S | 3/1998 | Geary et al. |
| 5,749,869 | A | 5/1998 | Lindenmeier et al. |
| 5,765,418 | A | 6/1998 | Rosenberg |
| 5,776,092 | A | 7/1998 | Farin et al. |
| 5,788,688 | A | 8/1998 | Bauer et al. |
| 5,797,907 | A | 8/1998 | Clement |
| 5,800,431 | A | 9/1998 | Brown |
| 5,836,897 | A | 11/1998 | Sakurai et al. |
| 5,836,909 | A | 11/1998 | Cosmescu |
| 5,836,944 | A | 11/1998 | Cosmescu |
| D402,030 | S | 12/1998 | Roberts et al. |
| D402,031 | S | 12/1998 | Roberts et al. |
| 5,843,109 | A | 12/1998 | Mehta et al. |
| 5,846,236 | A | 12/1998 | Lindenmeier et al. |
| 5,859,527 | A | 1/1999 | Cook |
| 5,868,768 | A | 2/1999 | Wicherski et al. |
| 5,876,400 | A | 3/1999 | Songer |
| 5,888,200 | A | 3/1999 | Walen |
| 5,893,848 | A | 4/1999 | Negus et al. |
| 5,893,849 | A | 4/1999 | Weaver |
| 5,893,862 | A | 4/1999 | Pratt et al. |
| 5,913,864 | A | 6/1999 | Garito et al. |
| 5,919,219 | A | 7/1999 | Knowlton |
| 5,928,159 | A | 7/1999 | Eggers et al. |
| 5,938,589 | A | 8/1999 | Wako et al. |
| 5,941,887 | A | 8/1999 | Steen et al. |
| 5,944,737 | A | 8/1999 | Tsonton et al. |
| 5,951,548 | A | 9/1999 | DeSisto et al. |
| 5,951,581 | A | 9/1999 | Saadat et al. |
| 5,954,686 | A | 9/1999 | Garito et al. |
| 5,972,007 | A | 10/1999 | Sheffield et al. |
| 6,004,318 | A | 12/1999 | Garito et al. |
| 6,004,333 | A | 12/1999 | Sheffield et al. |
| 6,004,335 | A | 12/1999 | Vaitekunas et al. |
| 6,010,499 | A | 1/2000 | Cobb |
| 6,022,347 | A | 2/2000 | Lindenmeier et al. |
| 6,045,564 | A | 4/2000 | Walen |
| 6,063,050 | A | 5/2000 | Manna et al. |
| 6,068,603 | A | 5/2000 | Suzuki |
| 6,068,627 | A | 5/2000 | Orszulak et al. |
| 6,070,444 | A | 6/2000 | Lontine et al. |
| 6,071,281 | A | 6/2000 | Burnside et al. |
| 6,074,386 | A | 6/2000 | Goble et al. |
| 6,074,387 | A | 6/2000 | Heim et al. |
| 6,086,544 | A | 7/2000 | Hibner et al. |
| 6,090,123 | A | 7/2000 | Culp et al. |
| 6,099,525 | A | 8/2000 | Cosmescu |
| 6,117,134 | A | 9/2000 | Cunningham et al. |
| 6,139,547 | A | 10/2000 | Lontine et al. |
| D433,752 | S | 11/2000 | Saravia |
| 6,142,995 | A | 11/2000 | Cosmescu |
| 6,146,353 | A | 11/2000 | Platt, Jr. |
| 6,149,648 | A | 11/2000 | Cosmescu |
| 6,156,035 | A | 12/2000 | Songer |
| 6,197,024 | B1 | 3/2001 | Sullivan |
| 6,200,311 | B1 | 3/2001 | Danek et al. |
| D441,077 | S | 4/2001 | Garito et al. |
| 6,213,999 | B1 | 4/2001 | Platt, Jr. et al. |
| 6,214,003 | B1 | 4/2001 | Morgan et al. |
| 6,238,388 | B1 | 5/2001 | Ellman et al. |
| 6,241,723 | B1 | 6/2001 | Heim et al. |
| 6,241,753 | B1 | 6/2001 | Knowlton |
| 6,249,706 | B1 | 6/2001 | Sobota et al. |
| 6,251,110 | B1 | 6/2001 | Wampler |
| 6,257,241 | B1 | 7/2001 | Wampler |
| 6,258,088 | B1 | 7/2001 | Tzonev et al. |
| 6,273,862 | B1 | 8/2001 | Privitera et al. |
| 6,277,083 | B1 | 8/2001 | Eggers et al. |
| 6,286,512 | B1 | 9/2001 | Loeb et al. |
| 6,287,305 | B1 | 9/2001 | Heim et al. |
| 6,287,344 | B1 | 9/2001 | Wampler et al. |
| 6,312,441 | B1 | 11/2001 | Deng |
| 6,325,799 | B1 | 12/2001 | Goble |
| D453,222 | S | 1/2002 | Garito et al. |
| D453,833 | S | 2/2002 | Hess |
| 6,350,276 | B1 | 2/2002 | Knowlton |
| 6,352,544 | B1 | 3/2002 | Spitz |
| 6,355,034 | B2 | 3/2002 | Cosmescu |
| 6,358,281 | B1 | 3/2002 | Berrang et al. |
| 6,361,532 | B1 | 3/2002 | Burek |
| D457,955 | S | 5/2002 | Bilitz |
| 6,386,032 | B1 | 5/2002 | Lemkin et al. |
| 6,395,001 | B1 | 5/2002 | Ellman et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,725 | B1 | 6/2002 | Khandkar et al. |
| 6,413,255 | B1 | 7/2002 | Stern |
| 6,416,491 | B1 | 7/2002 | Edwards et al. |
| 6,416,509 | B1 | 7/2002 | Goble et al. |
| 6,425,912 | B1 | 7/2002 | Knowlton |
| 6,458,122 | B1 | 10/2002 | Pozzato |
| 6,458,125 | B1 | 10/2002 | Cosmescu |
| 6,461,352 | B2 | 10/2002 | Morgan et al. |
| 6,464,702 | B2 | 10/2002 | Schulze et al. |
| 6,471,659 | B2 | 10/2002 | Eggers et al. |
| 6,494,882 | B1 | 12/2002 | Lebouitz et al. |
| 6,500,169 | B1 | 12/2002 | Deng |
| 6,511,479 | B2 | 1/2003 | Gentelia et al. |
| 6,526,320 | B2 | 2/2003 | Mitchell |
| 6,551,313 | B1 | 4/2003 | Levin |
| 6,558,383 | B2 | 5/2003 | Cunningham et al. |
| 6,585,664 | B2 | 7/2003 | Burdorff et al. |
| 6,589,239 | B2 | 7/2003 | Khandkar et al. |
| 6,610,054 | B1 | 8/2003 | Edwards et al. |
| 6,610,057 | B1 | 8/2003 | Ellman et al. |
| 6,616,658 | B2 | 9/2003 | Ineson |
| 6,618,626 | B2 | 9/2003 | West, Jr. et al. |
| 6,620,161 | B2 | 9/2003 | Schulze et al. |
| 6,632,193 | B1 | 10/2003 | Davison et al. |
| 6,652,514 | B2 | 11/2003 | Ellman et al. |
| 6,662,053 | B2 | 12/2003 | Borkan |
| 6,669,691 | B1 | 12/2003 | Taimisto |
| 6,685,701 | B2 | 2/2004 | Orszulak et al. |
| 6,685,704 | B2 | 2/2004 | Greep |
| 6,702,812 | B2 | 3/2004 | Cosmescu |
| 6,710,546 | B2 | 3/2004 | Crenshaw |
| 6,712,813 | B2 | 3/2004 | Ellman et al. |
| 6,719,746 | B2 | 4/2004 | Blanco |
| 6,740,079 | B1 | 5/2004 | Eggers et al. |
| 6,747,218 | B2 | 6/2004 | Huseman et al. |
| D493,530 | S | 7/2004 | Reschke |
| D493,888 | S | 8/2004 | Reschke |
| D494,270 | S | 8/2004 | Reschke |
| D495,051 | S | 8/2004 | Reschke |
| D495,052 | S | 8/2004 | Reschke |
| 6,794,929 | B2 | 9/2004 | Pelly |
| 6,830,569 | B2 | 12/2004 | Thompson et al. |
| 6,840,948 | B2 | 1/2005 | Albrecht et al. |
| 6,855,140 | B2 | 2/2005 | Albrecht et al. |
| 6,902,536 | B2 | 6/2005 | Manna et al. |
| 6,905,496 | B1 | 6/2005 | Ellman et al. |
| 6,923,804 | B2 | 8/2005 | Eggers et al. |
| 6,923,809 | B2 | 8/2005 | Eggers et al. |
| 6,939,347 | B2 | 9/2005 | Thompson |
| 6,955,674 | B2 | 10/2005 | Eick et al. |
| D515,412 | S | 2/2006 | Waaler et al. |
| 7,033,353 | B2 | 4/2006 | Stoddard et al. |
| D521,641 | S | 5/2006 | Reschke et al. |
| D535,396 | S | 1/2007 | Reschke et al. |
| 7,156,842 | B2 | 1/2007 | Sartor et al. |
| 7,156,844 | B2 | 1/2007 | Reschke et al. |
| 7,235,072 | B2 | 6/2007 | Sartor et al. |
| 7,241,294 | B2 | 7/2007 | Reschke |

| | | |
|---|---|---|
| 7,244,257 B2 | 7/2007 | Podhajsky et al. |
| 7,311,706 B2 | 12/2007 | Schoenman et al. |
| 7,393,354 B2 | 7/2008 | Buchman, II et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki et al. |
| 2004/0034346 A1 | 2/2004 | Stern et al. |
| 2004/0054370 A1 | 3/2004 | Given |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113817 A1 | 5/2005 | Isaacson et al. |
| 2005/0113818 A1 | 5/2005 | Sartor et al. |
| 2005/0113823 A1 | 5/2005 | Reschke |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0030034 A1* | 2/2006 | Mirizzi et al. ............ 606/50 |
| 2006/0041257 A1 | 2/2006 | Sartor et al. |
| 2006/0058783 A1 | 3/2006 | Buchman |
| 2006/0178667 A1 | 8/2006 | Sartor et al. |
| 2007/0049926 A1 | 3/2007 | Sartor |
| 2007/0093810 A1 | 4/2007 | Sartor |
| 2007/0142832 A1 | 6/2007 | Sartor |
| 2007/0260239 A1 | 11/2007 | Podhajsky et al. |
| 2007/0260240 A1 | 11/2007 | Rusin |

FOREIGN PATENT DOCUMENTS

| | | |
|---|---|---|
| DE | 24 60 481 A1 | 6/1976 |
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1656900 | 5/2006 |
| EP | 1645234 | 12/2006 |
| EP | 1852078 | 11/2007 |
| FR | 2235669 | 1/1975 |
| FR | 2798579 | 3/2001 |
| WO | WO 94/20032 | 9/1994 |
| WO | WO 96/39086 | 12/1996 |
| WO | WO 98/43264 | 10/1998 |
| WO | WO 01/64122 | 9/2001 |
| WO | WO 02/47568 A1 | 6/2002 |
| WO | WO 2004/010883 A1 | 2/2004 |
| WO | WO 2004/045436 A1 | 6/2004 |
| WO | WO 2004/073753 A2 | 9/2004 |
| WO | WO 2005/060849 A1 | 7/2005 |

OTHER PUBLICATIONS

International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from Ep 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).

* cited by examiner

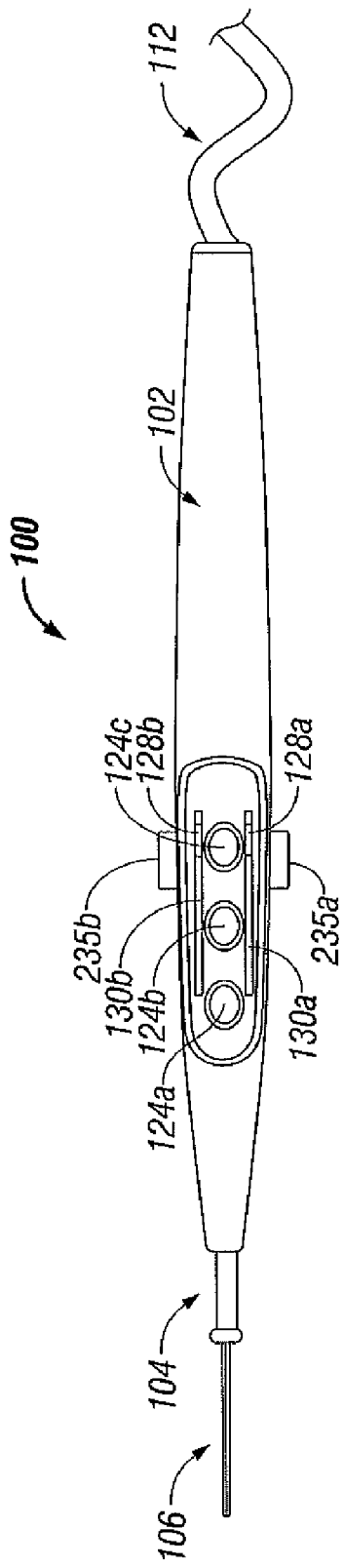
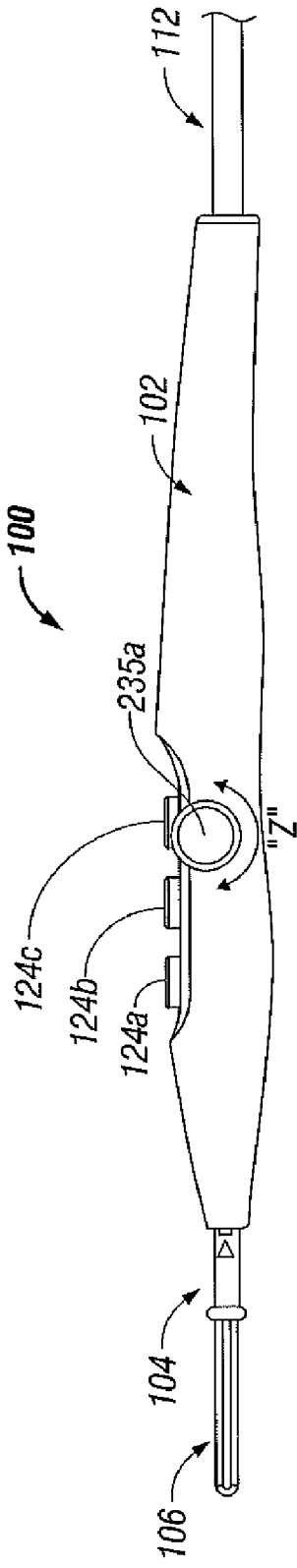
FIG. 5
FIG. 6

THERMAL PENETRATION AND ARC LENGTH CONTROLLABLE ELECTROSURGICAL PENCIL

CROSS-REFERENCE TO RELATED APPLICATIONS

This application claims the benefit of priority to U.S. Provisional Application Ser. No. 60/992,413 entitled "THERMAL PENETRATION AND ARC LENGTH CONTROLLABLE ELECTROSURGICAL PENCIL" filed Dec. 5, 2007 by Jason L. Craig, which is incorporated by reference herein.

BACKGROUND

1. Technical Field

The present disclosure relates generally to electrosurgical instruments and, more particularly, to an electrosurgical pencil having a plurality of hand-accessible variable controls.

2. Background of Related Art

Electrosurgical instruments have become widely used by surgeons in recent years. Accordingly, a need has developed for equipment and instruments that are easy to handle, are reliable and are safe in an operating environment. By and large, most electrosurgical instruments are hand-held instruments, e.g., an electrosurgical pencil, that transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

As used herein the term "electrosurgical pencil" is intended to include instruments having a handpiece that is attached to an active electrode and is used to cauterize, coagulate and/or cut tissue. Typically, the electrosurgical pencil may be operated by a handswitch or a foot switch. The active electrode is an electrically conducting element, which is usually elongated and may be in the form of a thin flat blade with a pointed or rounded distal end. Alternatively, the active electrode may include an elongated narrow cylindrical needle that is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) that produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect.

The power parameters are typically controlled from outside the sterile field, which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings. As can be appreciated, this gives the surgeon a great deal of variety when treating tissue. However, so many options also tend to complicate simple surgical procedures and may lead to confusion. Moreover, surgeons typically follow preset control parameters and stay within known modes, frequencies, and power settings.

SUMMARY

The present disclosure is directed to an electrosurgical pencil having variable controls. In accordance with one aspect of the present disclosure the electrosurgical pencil includes an elongated housing and an electrocautery electrode supported within the housing and extending distally from the housing, the electrocautery electrode being connected to a source of electrosurgical energy. At least one voltage divider network (hereinafter "VDN") is also supported on the housing and, is electrically connected to the source of electrosurgical energy for controlling a frequency, intensity, and/or mode of electrosurgical energy being delivered to the electrocautery electrode.

In another embodiment, an electrosurgical pencil is disclosed having an elongated housing and an electrocautery electrode supported within the housing and extending distally therefrom. The electrocautery electrode is operable to connect to a source of electrosurgical energy. At least one voltage divider network is supported on the housing and is operable to electrically connect to the source of electrosurgical energy for controlling the frequency, intensity, and/or mode of electrosurgical energy being delivered to the electrocautery electrode. The electrosurgical pencil further includes a frequency controller slidably supported on the housing. The frequency controller is configured to selectively actuate the voltage divider network(s) and provide a tactile feedback to a user of the electrosurgical pencil as the frequency controller is moved relative to the housing.

BRIEF DESCRIPTION OF THE DRAWINGS

Various embodiments of the present disclosure are described herein with reference to the drawings wherein:

FIG. 5 is a top plan view of an electrosurgical pencil according to another embodiment of the present disclosure;

FIG. 6 is a side elevational view of the electrosurgical pencil of FIG. 5;

DETAILED DESCRIPTION

Particular embodiments of the present disclosure are described hereinbelow with reference to the accompanying drawings. As used herein, the term "distal" refers to that portion which is further from the user while the term "proximal" refers to that portion which is closer to the user or surgeon. In the following description, well-known functions or constructions are not described in detail to avoid obscuring the present disclosure in unnecessary detail.

In general, the present disclosure is directed to an electrosurgical pencil including an electrocautery electrode and at least one VDN electrically connected to a source of electrosurgical energy for controlling at least one of a frequency, an intensity, and a mode of electrosurgical energy being delivered to the electrocautery electrode.

Figure 1:
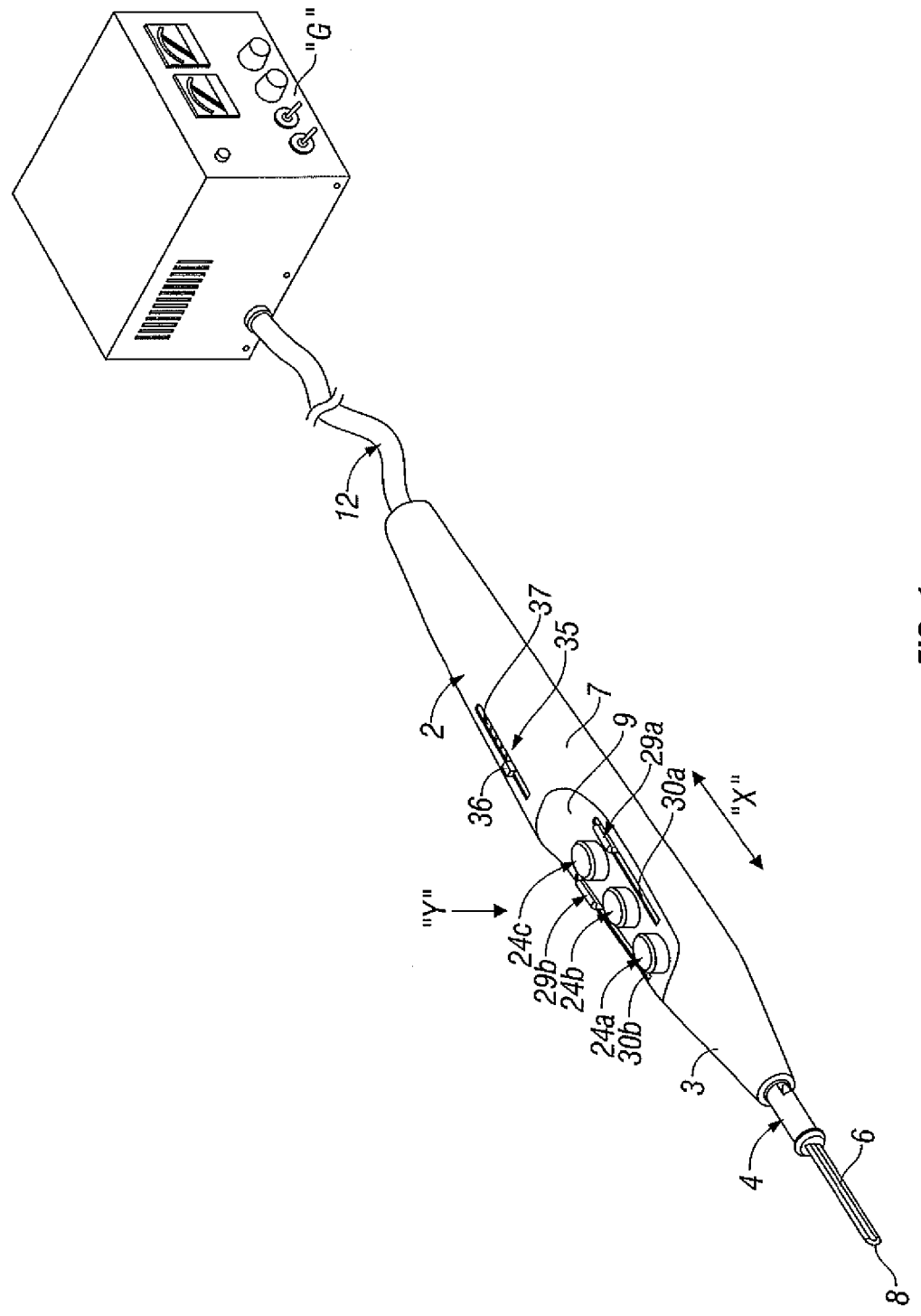
FIG. 1 is a perspective view of an electrosurgical pencil in accordance with the present disclosure.

FIG. 1 sets forth a perspective view of an electrosurgical pencil constructed in accordance with one embodiment of the present disclosure and generally referenced by numeral 10. While the following description will be directed towards electrosurgical pencils for the purposes of illustration, the features and concepts (or portions thereof) of the present disclosure can be applied to any electrosurgical type instrument, e.g., forceps, suction coagulator, vessel sealers, etc.

Figure 2A:
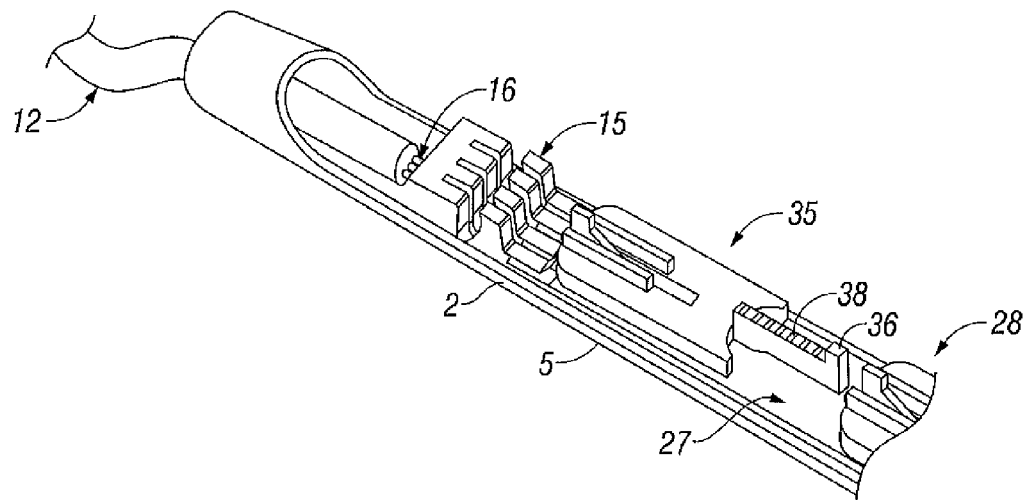
FIG. 2A is a partially exploded, perspective view of the proximal end of the electrosurgical pencil of FIG. 1.
Figure 2B:
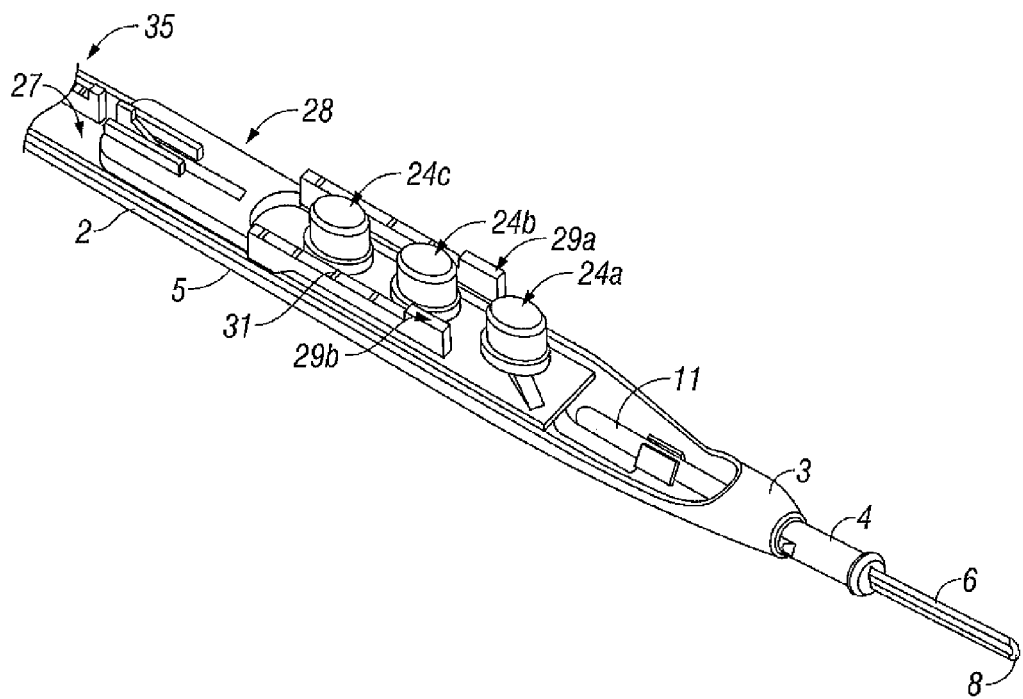
FIG. 2B is a partially exploded, perspective view of the distal end of the electrosurgical pencil of FIG. 1.
Figure 3:
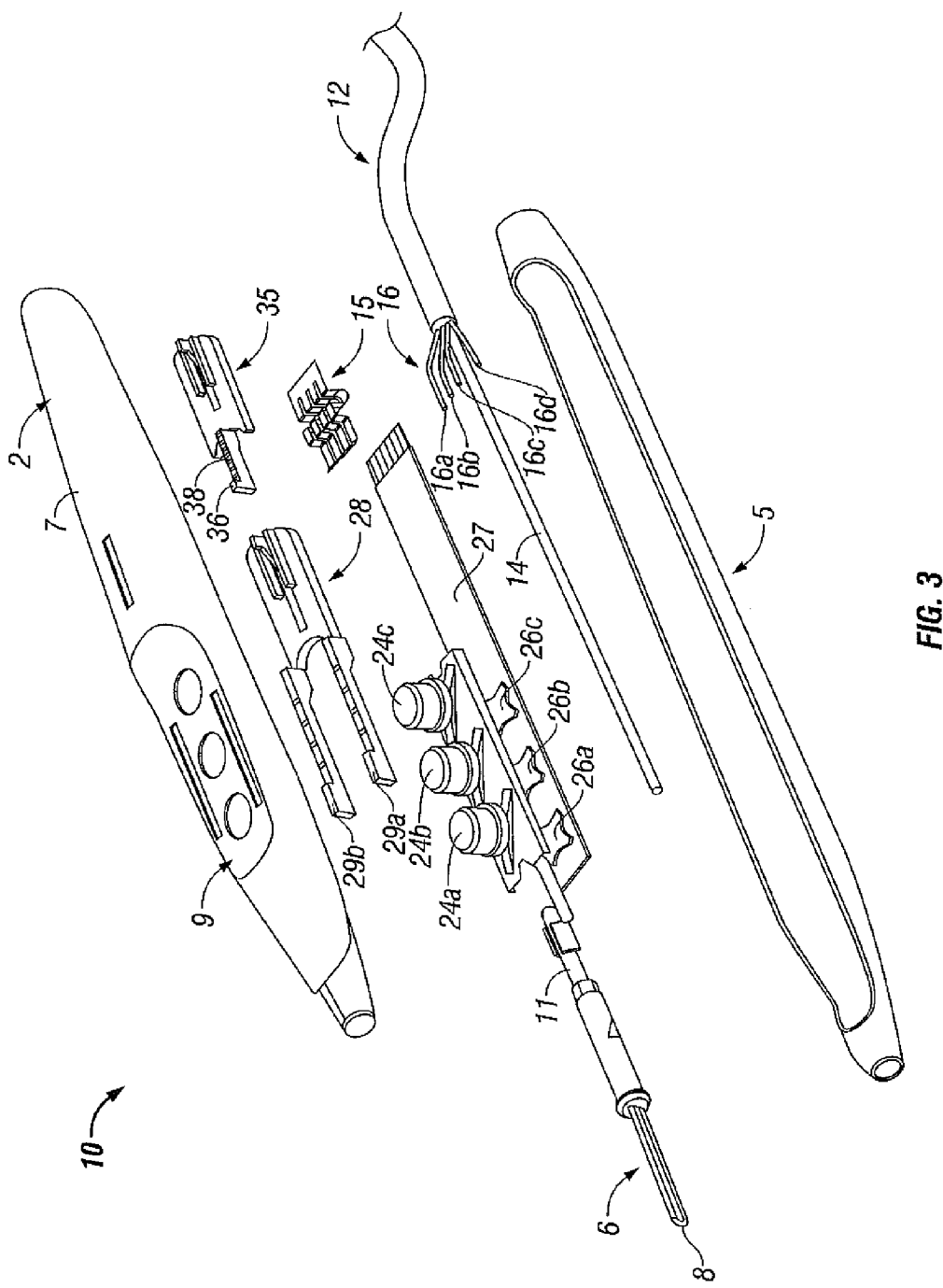
FIG. 3 is an exploded perspective view of the electrosurgical pencil of FIGS. 1 and 2.

As seen in FIGS. 1-3, electrosurgical pencil 10 includes an elongated housing 2 configured and adapted to support a blade receptacle 4 at a distal end 3 thereof which, in turn, receives a replaceable electrocautery end effector 6 in the form of a loop and/or blade therein. Electrocautery blade 6 is understood to include a planar blade, a loop, a needle and the like. A distal end portion 8 of blade 6 extends distally from receptacle 4 while a proximal end portion 11 (see FIG. 3) of blade 6 is retained within distal end 3 of housing 2. Electrocautery blade 6 may be fabricated from any suitable conductive type material, such as, for example, stainless steel, or is coated with an electrically conductive material.

As shown, electrosurgical pencil 10 is coupled to a conventional electrosurgical generator "G" via a cable 12. Cable 12 includes a transmission wire 14 (see FIG. 3), which electrically interconnects electrosurgical generator "G" with proximal end portion 11 of electrocautery blade 6. Cable 12 further includes control wires 16, which electrically interconnect mode activation switches (as will be described in greater detail below), supported on an outer surface 7 of housing 2, with electrosurgical generator "G". For the purposes herein the terms "switch" or "switches" includes electrical actuators, mechanical actuators, electro-mechanical actuators (rotatable actuators, pivotable actuators, toggle-like actuators, buttons, etc.) or optical actuators.

Turning back to FIGS. 1-3, as mentioned above, electrosurgical pencil 10 further includes at least one activation switch. In the illustrated embodiment, electrosurgical pencil 10 includes three activation switches 24a-24c, each of which are supported on an outer surface 7 of housing 2. Each activation switch 24a-24c is operatively connected to a location on a tactile element 26a-26c (e.g., a snap-dome is shown) which, in turn, controls the transmission of RF electrical energy supplied from generator "G" to electrosurgical blade 6. More particularly, tactile elements 26a-26c are operatively connected to a voltage divider network 27 (hereinafter "VDN 27"), which forms a switch closure (e.g., here shown as a film-type potentiometer). For the purposes herein, the term "voltage divider network" relates to any known form of resistive, capacitive or inductive switch closure (or the like) that determines the output voltage across a voltage source (e.g., one of two impedances) connected in series. A "voltage divider" as used herein relates to a number of resistors connected in series that are provided with taps at certain points to make available a fixed or variable fraction of the applied voltage.

In use, depending on which activation switch 24a-24c is depressed a respective switch 26a-26c is pressed into contact with VDN 27 and a characteristic signal is transmitted to electrosurgical generator "G" via control wires 16. Control wires 16a-16c are electrically connected to switches 26a-26c via a terminal 15 (see FIGS. 2 and 3) operatively connected to VDN 27. In embodiments, electrosurgical generator "G" may be used in conjunction with the device wherein generator "G" includes a circuit for interpreting and responding to the VDN settings.

Activation switches 24a-24c are configured and adapted to control the mode and/or "waveform duty cycle" to achieve a desired surgical intent. For example, first activation switch 24a can be set to deliver a characteristic signal to electrosurgical generator "G" that in turn transmits a duty cycle and/or waveform shape that produces a cutting and/or dissecting effect/function. Meanwhile, second activation switch 24b can be set to deliver a characteristic signal to electrosurgical generator "G" that in turn transmits a duty cycle and/or waveform shape that produces a blending effect/function (e.g., a combination of a dissecting and a hemostatic effect/function). Finally, third activation switch 24c can be set to deliver a characteristic signal to electrosurgical generator "G" that in turn transmits a duty cycle and/or waveform shape that produces a hemostatic effect/function.

Fourth control wire 16d (i.e., a return control wire) is connected to proximal end 11 of electrocautery blade 6. This prevents electrosurgical current, induced in control wires 16a-16c, from flowing through activation switches 24a-24c to electrocautery blade 6. This in turn, increases the longevity and life of switches 24a-24c.

Electrosurgical pencil 10 further includes an intensity controller 28 slidingly supported on housing 2. Intensity controller 28 includes a pair of nubs 29a, 29b, which are slidingly supported, one each, in respective guide channels 30a, 30b, formed in outer surface 7 of housing 2 on either side of activations switches 24a-24c. By providing nubs 29a, 29b on either side of activation switches 24a-24c, controller 28 can be easily manipulated by either hand of the user or the same electrosurgical pencil can be operated by a right-handed or a left-handed user.

In embodiments, intensity controller 28 may be a slide potentiometer wherein nubs 29a, 29b have a first position (e.g., proximal-most position closest to cable 12) corresponding to a relative low intensity setting, a second position (e.g., a distal-most position closest to electrocautery end effector 6) corresponding to a relative high intensity setting, and a plurality of intermediate positions corresponding to intermediate intensity settings. In embodiments, the intensity settings from proximal end to distal end may be reversed (e.g., high to low). Nubs 29a, 29b of intensity controller 28 and corresponding guide channels 30a, 30b may be provided with a series of cooperating discreet or dented positions defining a series of positions (e.g., five) to allow easy selection of the output intensity from the low intensity setting to the high intensity setting. The series of cooperating discreet or detented positions also provide the surgeon with a degree of tactile feedback. As best seen in FIG. 2, intensity controller 28 can include a series of indicia 31 provided thereon, which are visible through guide channels 30a, 30b. Indicia 31 may be a series of numbers (e.g., numbers 1-5) that reflect the level of intensity that is to be transmitted. Alternatively, level indicators may be printed alongside the sides of guide channels 30a, 30b along which nubs 29a, 29b slide.

Intensity controller 28 is configured and adapted to adjust the power parameters (e.g., voltage, power and/or current intensity) and/or the power verses impedance curve shape to affect the perceived output intensity. For example, the greater intensity controller 28 is displaced in a distal direction the greater the level of the power parameters transmitted to electrocautery blade 6. Conceivably, current intensities can range from about 60 mA to about 240 mA when using an electrosurgical blade and having a typical tissue impedance of about 2K ohms. An intensity level of 60 mA provides very light and/or minimal cutting/dissecting/hemostatic effects. An intensity level of 240 mA provides very aggressive cutting/dissecting/hemostatic effects. Accordingly, the optimal range of current intensity is from about 100 mA to about 200 mA at 2K ohms.

In embodiments, the intensity settings are preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

Electrosurgical pencil 10 further includes a frequency controller 35 slidingly supported on housing 2. Frequency controller 35 includes a nub 36 that is slidingly supported in a guide channel 37 formed in outer surface 7 of housing 2 proximal to activation switches 24a-24c.

In embodiments, frequency controller 35 may be a slide potentiometer wherein nub 36 has a first position (e.g., a proximal-most position closest to cable 12) corresponding to a relative low frequency setting, a second position (e.g., a distal-most position closest to electrocautery end effector 6) corresponding to a relatively high frequency setting, and a plurality of intermediate positions corresponding to intermediate frequency settings. Any one of the plurality of intermediate positions may correspond to the "park" position, as discussed above, that corresponds to a standard and/or predetermined frequency setting.

In embodiments, nub 36 of frequency controller 35 and corresponding guide channel 37 may be provided with a series of cooperating discreet or dented positions defining a series of positions (e.g., five positions) to allow easy selection of the output frequency from the low frequency setting to the high frequency setting. The series of cooperating discreet or detented positions also provide the surgeon with a degree of tactile feedback. As best seen in FIG. 2, frequency controller 35 may include a series of indicia 38 provided thereon that are visible through guide channel 37, Indicia 38 may be a series of numbers (e.g., numbers 1-5) that reflect the level of frequency that is to be transmitted. Alternatively, level indicators may be printed alongside the side of guide channel 37 along which nub 36 slides.

Frequency controller 35 is configured and adapted to adjust the frequency parameter to affect the perceived RF output of generator "G." By way of example, the greater frequency controller 35 is displaced in a distal direction the greater the level of the frequency parameter of the energy transmitted to electrocautery blade 6. As frequency is increased from about 470 kHz to about 1 MHz, thermal penetration decreases and arc length increases. Thus, a frequency level of 470 kHz provides for deep thermal penetration and a relatively short arc length while a frequency level of 1 MHz provides for superficial thermal penetration and a relatively long arc length. Accordingly, the user would utilize the frequency controller 35 to select the lower 470 kHz level of frequency if deep thermal penetration is required to provide the desired surgical effect without the need for a long arc length. Conversely, the user would utilize the frequency controller 35 to select the higher 1 MHz level of frequency if superficial thermal penetration and a longer arc length are required to provide the desired surgical effect.

In embodiments, the frequency settings may be preset and selected from a look-up table based on a choice of electrosurgical instruments/attachments, desired surgical effect, surgical specialty and/or surgeon preference. The selection may be made automatically or selected manually by the user. The frequency values may be predetermined or adjusted by the user.

Figure 12:
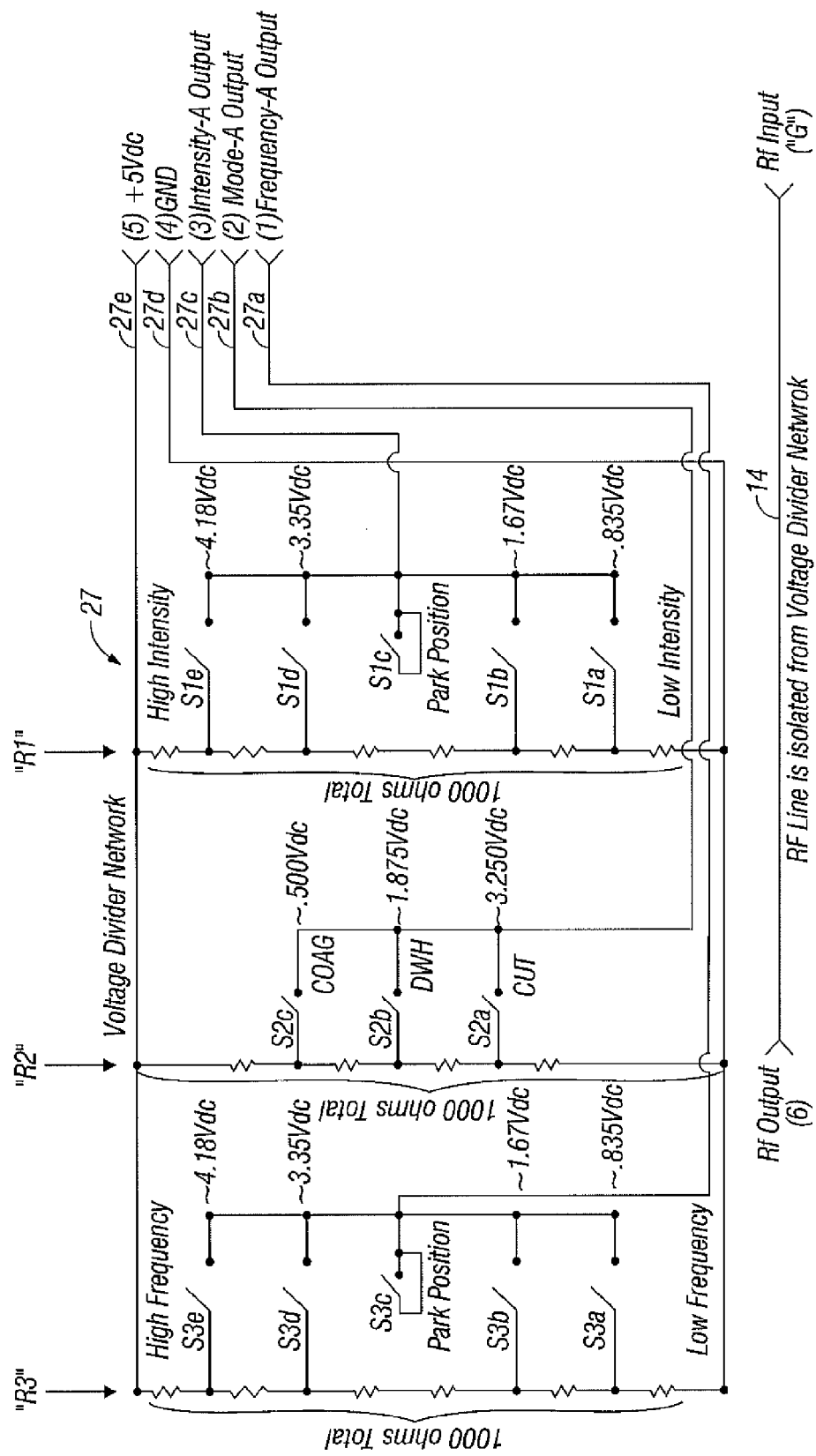
FIG. 12 is a schematic illustration of a voltage divider network according to an embodiment of the present disclosure.

With reference to FIG. 12, in accordance with an embodiment of the present disclosure, a voltage divider network (VDN) 27, for inter-connecting control wires 16a-16d to activation and electrosurgical switches 24a-24c and electrocautery power wire 14 to blade 6, is shown. VDN 27 includes a first transmission line 27a, electrically connected to one of control wires 16a-16d, to operate the various frequencies of electrosurgical pencil 10. VDN 27 includes a second transmission line 27b, electrically connected to one of control wires 16a-16d, to operate the various modes of electrosurgical pencil 10. VDN 27 includes a third transmission line 27c, electrically connected to one of control wires 16a-16d, to operate the various intensities of electrosurgical pencil 10. VDN 27 includes a fourth and fifth transmission line 27d and 27e, respectively, to apply a voltage across VDN 27. For example, fourth transmission line 27d may be isolated or grounded and transmission line 27e may transmit +5 volts.

In the illustrated embodiment, VDN 27 includes a plurality of resistors "R1" (e.g., 6 resistors), connected in a first series between transmission line 27d and transmission line 27e. In embodiments, resistors "R1" may combine to total about 1000 ohms of resistance. The first series of resistors "R1" is selectively actuatable by intensity controller 28 at a plurality of locations along the length thereof. These locations along the length of the first series of resistors "R1" are represented as a first set of switches "S1a-S1e." In operation, as intensity controller 28 is moved along the first series of resistors "R1," the value of the resistance of the first series of resistors "R1" is changed. The change of the resistance value of the first series of resistors "R1" is represented in FIG. 12 as the closing of a switch "S1a-S1e." The change in resistance of the first series of resistors "R1" causes a change in voltage that is measured by electrosurgical generator "G" that, in turn, transmits an RF energy at a unique intensity to electrosurgical pencil 10.

When intensity controller 28 is moved to a third of middle position along the first series of resistors "R1," corresponding to switch "S1c," a "park position" is established in which no resistance is present. Accordingly, electrosurgical generator "G" measures a maximum voltage value of zero volts.

VDN 27 further includes a plurality of resistors "R2" (e.g., four resistors), connected in a second series between transmission line 27d and transmission line 27e. In embodiments, resistors "R2" may combine to total about 1000 ohms of resistance. The second series of resistors "R2" is selectively actuatable by any one of activation buttons 24a-24c. The location where the second series of resistors "R2" is actuated is represented by as a second set of switches "S2a-S2c." In operation, depending which switch "S2a-S2c" is closed, by actuation of a particular activation switch 24a-24c, the value of the resistance of the second series of resistors "R2" is changed. The change of the resistance value of the second series of resistors "R2" causes a change in voltage that is measured by electrosurgical generator "G" that, in turn, activates and transmits a different mode of operation to electrosurgical pencil 10.

VDN 27 further includes a plurality of resistors "R3" (e.g., six resistors), connected in a third series between transmission line 27d and transmission line 27e. In embodiments, resistors "R3" may combine to total about 1000 ohms of resistance. The third series of resistors "R3" is selectively actuatable by frequency controller 35 at a plurality of locations along the length thereof. These locations along the length of the third series of resistors "R3" are represented as a third set of switches "S3a-S3e." In operation, as frequency controller 35 is moved along the third series of resistors "R3," the value of the resistance of the third series of resistors "R3" is changed. The change of the resistance value of the third series of resistors "R3" is represented in FIG. 12 as the closing of a switch "S3a-S3e." The change in resistance of the third series of resistors "R3" causes a change in voltage that is measured by electrosurgical generator "G" that, in turn, transmits an RF energy at a unique intensity to electrosurgical pencil 10.

When frequency controller 35 is moved to a third of middle position along the third series of resistors "R3," corresponding to switch "S3c," a "park position" is established in which no resistance is present. Accordingly, electrosurgical generator "G" measures a maximum voltage value of zero volts. In embodiments, electrosurgical generator "G" may interpret a measured voltage value of zero volts as a signal to transmit RF energy at a standard and/or predetermined level to electrosurgical pencil 10.

In operation, if more than one activation button 24a-24c is actuated simultaneously (i.e., a "multi-key activation" scenario), electrosurgical generator "G" will measure a unique voltage that does not correspond to any preset known voltage stored therein and thus does not activate or transmit any mode of operation to electrosurgical pencil 10.

In use, depending on which activation button 24a-24c is depressed a respective switch 26a-26c is pressed into contact with VDN 27. The depressed activation button 24a-24c electrically engages juxtaposed electrical contacts of VDN 27 thereby changing the value of the second series of resistors "R2." Depending on the value of the resistance of the second series of resistors "R2" a characteristic voltage is generated and measured by electrosurgical generator "G" via transmission line 27b and one of control wires 16a-16d. (See FIGS. 3 and 12).

In order to vary the intensity of the power parameters of electrosurgical pencil 10, the surgeon displaces intensity controller 28 as described above, thereby changing the value of the first series of resistors "R1." Depending on the value of the resistance of the first series of resistors "R1," a characteristic voltage is generated and measured by electrosurgical generator "G" via third transmission line 27c and one of control wires 16a-16d. (See FIGS. 3 and 12).

In embodiments, a VDN (not explicitly shown) separate from VDN 27 may be provided for any one of the first series, second series, and third series of resistors "R1," "R2," and "R3" or any combination thereof. In this configuration, an independent voltage comparator circuit (not explicitly shown) may be provided to permit bi-directional communication between two or more VDNs. In this manner, each VDN may reference the voltage and, thus, the unique mode/frequency/duty cycle of the RF energy being transmitted to electrocautery blade 6.

Also as depicted in FIG. 12, transmission wire 14 is isolated from or otherwise completely separate from VDN 27. In particular, transmission wire 14 extends directly from the RF input or generator "G" to the RF output or to electrocautery blade 6.

The hemostatic effect/function may be defined as having waveforms with a duty cycle from about 1% to about 12%. The blending effect/function may be defined as having waveforms with a duty cycle from about 12% to about 75%. The cutting and/or dissecting effect/function may be defined as having waveforms with a duty cycle from about 75% to about 100%. It is important to note that these percentages are approximated and may be customized to deliver the desired surgical effect for various tissue types and characteristics.

In operation and depending on the particular electrosurgical function desired, the surgeon depresses one of activation switches 24a-24c, in the direction indicated by arrow "Y" (see FIG. 1) thereby urging a corresponding switch 26a-26c against VDN 27 and thereby transmitting a respective characteristic signal to electrosurgical generator "G". For example, the surgeon can depress activation switch 24a to perform a cutting and/or dissecting function, activation switch 24b to perform a blending function, or activation switch 24c to perform a hemostatic function. In turn, generator "G" transmits an appropriate waveform output to electrocautery blade 6 via transmission wire 14.

In order to vary the intensity of the power parameters of electrosurgical pencil 10, the surgeon displaces intensity controller 28 in the direction indicated by double-headed arrow "X". As mentioned above, the intensity can be varied from approximately 60 mA for a light effect to approximately 240 mA for a more aggressive effect. For example, by positioning nubs 29a, 29b of intensity controller 28 closer to the proximal-most end of guide channels 30a, 30b (i.e., closer to cable 12) a lower intensity level is produced and by positioning nubs 29a, 29b of intensity controller 28 closer to the distal-most end of guide channels 30a, 30b (i.e., closer to electrocautery end effector 6) a larger intensity level is produced resulting in a more aggressive effect being produced. In embodiments, when nubs 29a, 29b of intensity controller 28 are positioned at the proximal-most end of guide channels 30a, 30b, VDN 27 is set to a null and/or open position. Electrosurgical pencil 10 may be shipped with intensity controller 28 set to the null and/or open positions. In embodiments, the frequency settings from proximal end to distal end may be reversed (e.g., high to low).

In order to vary the frequency of the energy transmitted by electrosurgical generator "G" to pencil 10, the surgeon displaces frequency controller 35 in the direction indicated by double headed arrow "X." As mentioned above, the frequency may be varied from about 1 MHz for superficial thermal penetration and a long arc length and 470 kHz for deep thermal penetration and a short arc length. For example, by positioning nub 36 of frequency controller 35 closer to the distal-most end of guide channel 37 (i.e., closer to electrocautery end effector 6) a higher frequency level is produced and by positioning nub 36 of frequency controller 35 closer to the distal-most end of guide channel 37 (i.e., closer to cable 12) a lower frequency level is produced resulting in deeper thermal penetration. In embodiments, when nub 36 of frequency controller 35 is positioned at the proximal-most end of guide channel 37, VDN 27 is set to a null and/or open position. Electrosurgical pencil 10 may be shipped with frequency controller 35 set to the null and/or open position.

In embodiments, intensity controller 28 may control the intensity level of the electrosurgical energy transmitted by all three activation switches 24a-24c, simultaneously. That is, as nubs 29a, 29b of intensity controller 28 are positioned relative to guide channels 30a, 30b, the intensity level of the electrosurgical energy transmitted to all three activation switches 24a-24c is set to the same value of slide potentiometer or intensity controller 28. Similarly, frequency controller 35 may control the frequency level of the electrosurgical energy transmitted by all three activation switches 24a-24c, simultaneously. That is, as nub 36 of frequency controller 35 is positioned relative to guide channel 37, the frequency level of the electrosurgical energy transmitted to all three activation switches 24a-24c is set to the same value of slide potentiometer or frequency controller 35.

As a safety precaution, when electrosurgical pencil 10 is changed from one mode to another, intensity controller 28 and frequency controller 35 may be configured such that each must be reset (i.e., nubs 29a, 29b, 36 re-positioned to the proximal-most end of guide channels 30a, 30b, 37, thus setting VDN 27 to the null and/or open position). After being reset, intensity controller 28 and frequency controller 35 may be adjusted as needed to the desired and/or necessary intensity level and frequency level respectively, for the mode selected.

In embodiments, VDN 27 may also include an algorithm that stores the last intensity level and/or frequency level setting for each mode. In this manner, intensity controller 28 and frequency controller 35 do not have to be reset to the last operative value when the particular mode is re-selected.

The combination of placing VDN 27 and fourth control wire 16d in electrosurgical pencil 10 essentially places the entire resistor network of the electrosurgical system (e.g., electrosurgical pencil 10 and the source of electrosurgical energy "G") within electrosurgical pencil 10. Conventional electrosurgical systems typically include a current limiting resistor disposed within the electrosurgical pencil, for activating the electrosurgical pencil, and a second resistor network disposed in the source of electrosurgical energy, for controlling the intensity of the electrosurgical energy transmitted. In accordance with the present disclosure, all three resistor networks are disposed within electrosurgical pencil 10, namely, the first resistor network as evidenced by frequency controller 35, the second resistor network as evidenced by activation switches 24a-24c, and the third resistor network as evidenced by intensity controller 28.

As described above, intensity controller 28 and frequency controller 35 can be configured and adapted to provide a degree of tactile feedback. Alternatively, audible feedback can be produced from intensity controller 28 (e.g., a "click"), from electrosurgical energy source "G" (e.g., a "tone") and/or from an auxiliary sound-producing device such as a buzzer (not explicitly shown).

As seen in FIGS. 1 and 3, intensity controller 28 and activation switches 24a-24c are supported in a recess 9 formed in outer wall 7 of housing 2. In embodiments, activation switches 24a-24c may be positioned at a location where the fingers of the surgeon would normally rest when electrosurgical pencil 10 is held in the hand of the surgeon while nubs 29a, 29b of intensity controller 28 are placed at locations that would not be confused with activation switches 24a-24c. Alternatively, nubs 29a, 29b of intensity controller 28 are positioned at locations where the fingers of the surgeon would normally rest when electrosurgical pencil 10 is held in the hand of the surgeon while activation switches 24a-24c are placed at locations that would not be confused with nubs 29a, 29b of intensity controller 28. In addition, recess 9 formed in outer wall 7 of housing 2 advantageously minimizes inadvertent activation (e.g., depressing, sliding and/or manipulating) of activation switches 24a-24c and intensity controller 28 while in the surgical field and/or during the surgical procedure. In embodiments, frequency controller 35 may be embodied in a "two-nub" configuration substantially similar to intensity controller 28. Likewise, intensity controller 28 may be embodied in a "single-nub" configuration substantially similar to frequency controller 35. In this configuration, the placement of frequency controller 35 and intensity controller 28 may be reversed. That is, frequency controller 35 may be supported within outer surface 7 of housing 2 on either side of activations switches 24a-24c (e.g., in guide channels 30a and 30b) and intensity controller 28 may be slidingly supported proximal to recess 9 (e.g., in guide channel 37). Additionally or alternatively, a second guide channel (not explicitly shown) may be formed in outer surface 7 of housing 2 proximal to activation switches 24a-24c. The second guide channel may be positioned in parallel to guide channel 37 and in spaced relation thereto (e.g., similar to guide channels 30a and 30b) to cooperatively support a "two-nub" embodiment of either intensity controller 28 or frequency controller 35.

As seen in FIG. 3, electrosurgical pencil 10 includes a molded/contoured hand grip 5, which substantially surrounds the distal and proximal ends of housing 2 as well as the underside of housing 2. Contoured hand grip 5 is shaped and dimensioned to improve the handling of electrosurgical pencil 10 by the surgeon. Accordingly, less pressure and gripping force is required to use and/or operate electrosurgical pencil 10 thereby potentially reducing the fatigue experienced by the surgeon and to prevent movement of electrosurgical pencil 10 during proximal and distal adjustments of nubs 29a and 29b.

Figure 4:
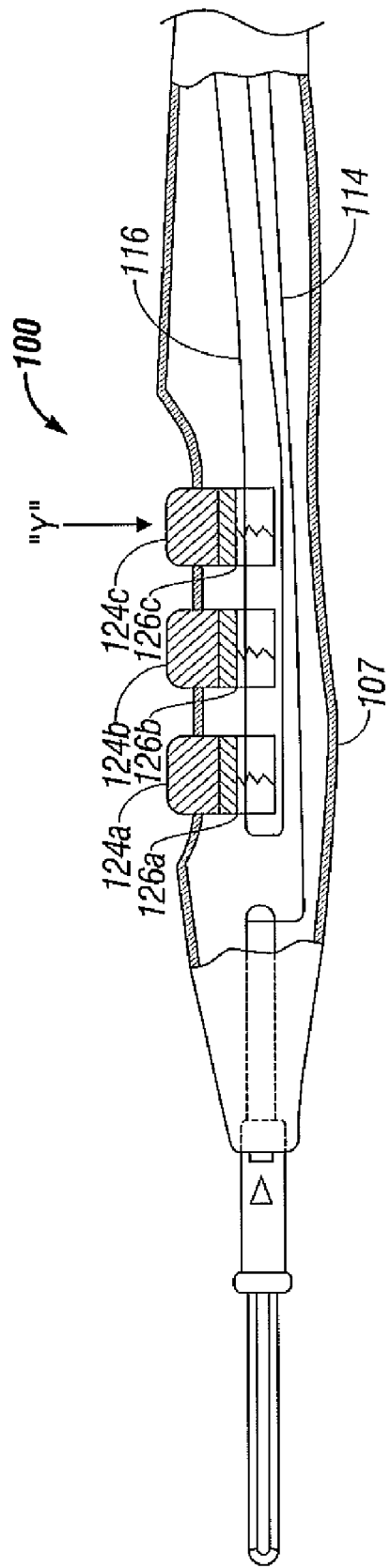
FIG. 4 is a partially exploded, side elevational view of an alternative embodiment of the electrosurgical pencil of FIGS. 1-3.

As seen in FIG. 4, an alternative embodiment of electrosurgical pencil 10 is shown generally as 100. Electrosurgical pencil 100 is similar to electrosurgical pencil 10 and will only be discussed in detail to the extent necessary to identify differences in construction and operation. As seen in FIG. 4, electrosurgical pencil 100 includes a plurality of activation switches 124a-124c, each of which are supported on an outer surface 107 of housing 102. Each activation switch 124a-124c is operatively connected to a respective switch 126a-126c which, in turn, controls the transmission of RF electrical energy supplied from generator "G" to electrosurgical blade 106. More particularly, switches 126a-126c are electrically coupled to control loop 116 and are configured to close and/or complete control loop 116 to thereby permit RF energy to be transmitted to electrocautery blade 106 from electrosurgical generator "G."

Activation switches 124a-124c are configured and adapted to control the mode and/or "waveform duty cycle" to achieve a desired surgical intent in the same manner as activation switches 24a-24c of electrosurgical pencil 10 described above.

In operation and depending on the particular electrosurgical function desired, the surgeon depresses one of activation switches 124a-124c, in the direction indicated by arrow "Y" thereby closing a corresponding switch 126a-126c and closing and/or completing control loop 116. For example, the surgeon can depress activation switch 124a to perform a cutting or dissecting function, activation switch 124b to perform a dissecting/hemostatic function, or activation switch 124c to perform a hemostatic function. In turn, generator "G" transmits an appropriate waveform output to electrocautery blade 106 via transmission wire 114.

In an alternative embodiment, as seen in FIGS. 5 and 6, sliding frequency controller 135 has been replaced with frequency controllers 235a, 235b in the form of dial-like VDNs. Frequency controllers 235a, 235b function to vary the frequency of the RF energy waveform via a rotation of dial controllers 235a, 235b in either a clockwise or counter-clockwise direction as indicated by double headed arrow "Z". As seen in FIGS. 5 and 6, dial controllers 235a, 235b are disposed externally of housing 102, however, dial controllers 235a, 235b may be disposed within housing 102 with only a portion projecting therefrom for manipulation by the surgeon. In embodiments, frequency controllers 235a, 235b may be a single controller having a pair of opposed knobs/dials provided, one each, on either side of housing 102. In this manner, the frequency can be controlled from either side of electrosurgical pencil 100. In the illustrated embodiment, frequency controllers 235a, 235b are shown positioned adjacent activation switches 124a-124c for illustrative purposes only and may be positioned anywhere along housing 102 (e.g., proximal or distal to activation switches 124a-124c). Further, sliding intensity controllers 128a, 128b may be slidably supported in guide channels 130a and 130b. Alternatively, intensity controllers 128a, 128b may be configured in either a "single-nub" or "double-nub" configuration and slidably supported in a guide channel (not explicitly shown) proximal or distal to activation switches 124a-124c.

In alternative embodiments, sliding intensity controllers 128a, 128b may be replaced with dial-like VDNs (not explicitly shown). In this configuration, sliding frequency controller 135 may be configured in either a "single-nub" or "double-nub" configuration and slidably supported in a guide channel (not explicitly shown) proximal or distal to activation switches 124a-124c.

Since the surgeon has a number of controls at his finger tips, the surgeon is able to create a pallet of varying therapeutic effects ranging from a pure "cutting" effect to a pure "coagulating" effect and a number of effects in between at a number of intensities and/or frequencies. Moreover, with some pre-setting of the electrosurgical energy source "G", electrosurgical pencil 100 will have all the useful settings available to the surgeon within the sterile field. Accordingly, it is not necessary that the surgeon interact with hardware outside the sterile field (e.g., electrosurgical energy source "G") once the surgical procedure begins thus allowing the surgeon to focus attention on the surgical procedure.

While embodiments of electrosurgical pencils according to the present disclosure have been described herein, it is not intended that the disclosure be limited there and the above description should be construed as merely exemplifications of preferred embodiments. Those skilled in the art will envision other modifications within the scope and spirit of the present disclosure.

Figure 7:
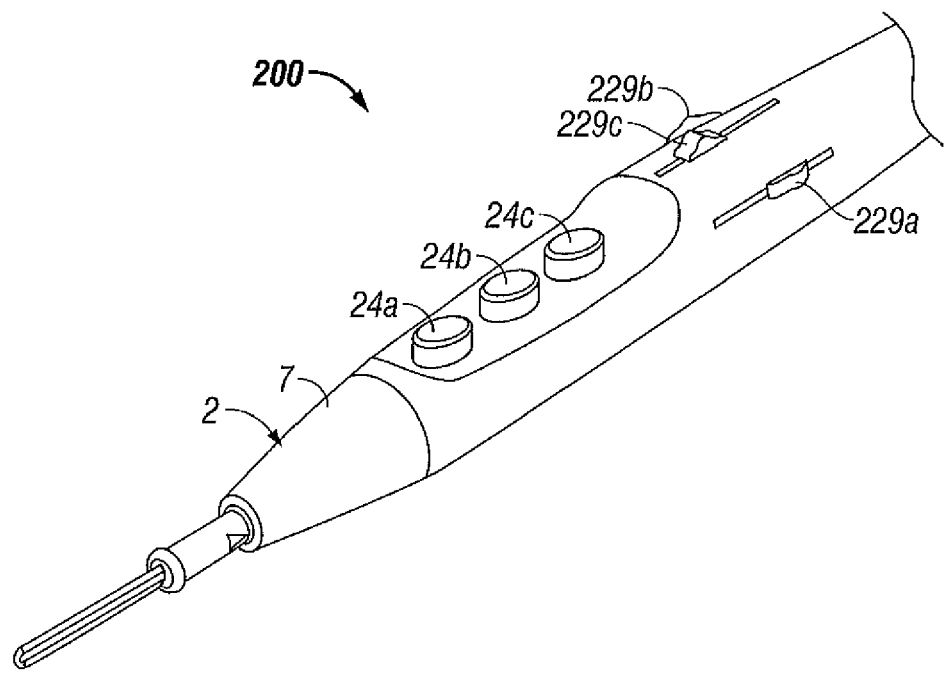
FIG. 7 is a front perspective view of a distal end portion of an electrosurgical pencil according to yet another embodiment of the present disclosure.

For example, as seen in FIG. 7, an alternative embodiment of an electrosurgical pencil is shown generally as 200. Electrosurgical pencil 200 is similar to electrosurgical pencil 10 and/or 100 and will only be discussed in detail to the extent necessary to identify differences in construction and operation. As seen in FIG. 7, electrosurgical pencil 200 includes a plurality of nubs 229a-229c, which are slidingly supported, one each, in respective guide channels 230a-230c, formed in outer surface 7 of housing 2, at a position proximal of activation switches 24a-24c. In embodiments, each nub 229a-229c is operatively engaged with a slide potentiometer and may be configured and adapted to adjust the frequency parameter to affect the perceived RF output of generator "G." In an alternative embodiment, each nub 229a-229c is operatively engaged with a slide potentiometer and may be configured and adapted to adjust the power parameters and/or the power verses impedance curve shape to affect the perceived output intensity.

Accordingly, electrosurgical pencil 200 can be configured such that each activation switch 24a-24c is a separate mode, such as, for example, activation switch 24a can be set such that electrosurgical pencil 200 performs "division" when depressed, activation switch 24b can be set such that electrosurgical pencil 200 performs "division with hemostasis" when depressed, and activation switch 24c can be set such that electrosurgical pencil 200 performs "hemostasis" when depressed. In addition, each of nubs 229a-229c is in operative engagement with a corresponding activation switch 24a-24c such that the power/frequency for each mode of operation of electrosurgical pencil 200 can be independently adjusted.

Figure 8:
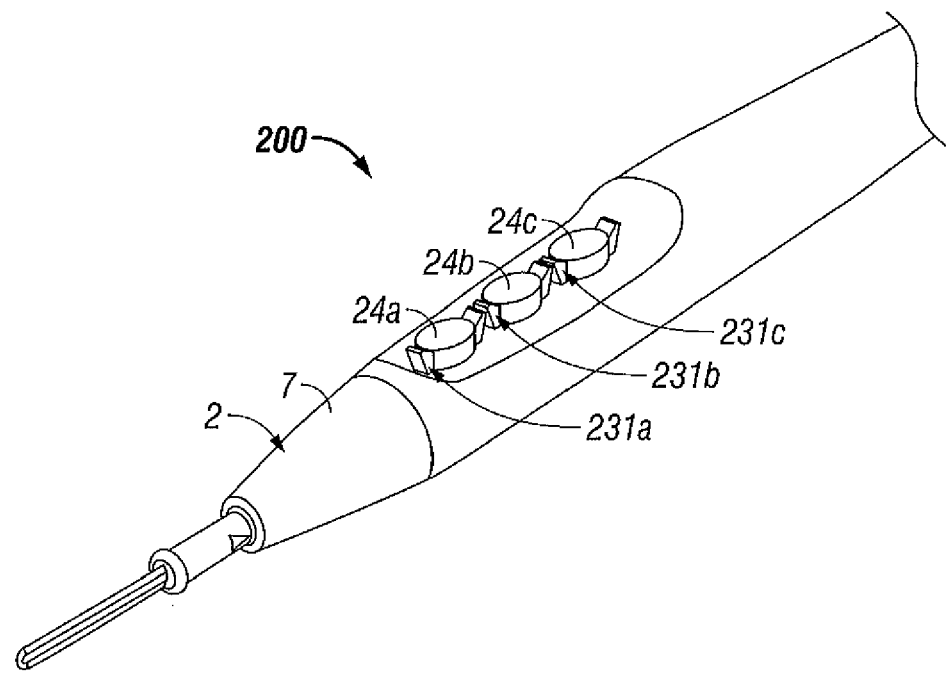
FIG. 8 is a front perspective view of a distal end portion of an electrosurgical pencil according to still another embodiment of the present disclosure.

As seen in FIG. 8, nubs 229a-229c of electrosurgical pencil 200 have been replaced with toggles 231a-231c operatively engaged with a respective activation switch 24a-24c. Each toggle 231a-231c can be operatively engaged with a rocker-type switch (not shown) or a rotational dial (not shown) in place of the slide-type potentiometer described above. Further, toggles 231a-231c may be configured and adapted to adjust the power parameters or, alternatively, the frequency parameters to adjust the perceived output intensity and perceived output frequency, respectively.

Figure 9:
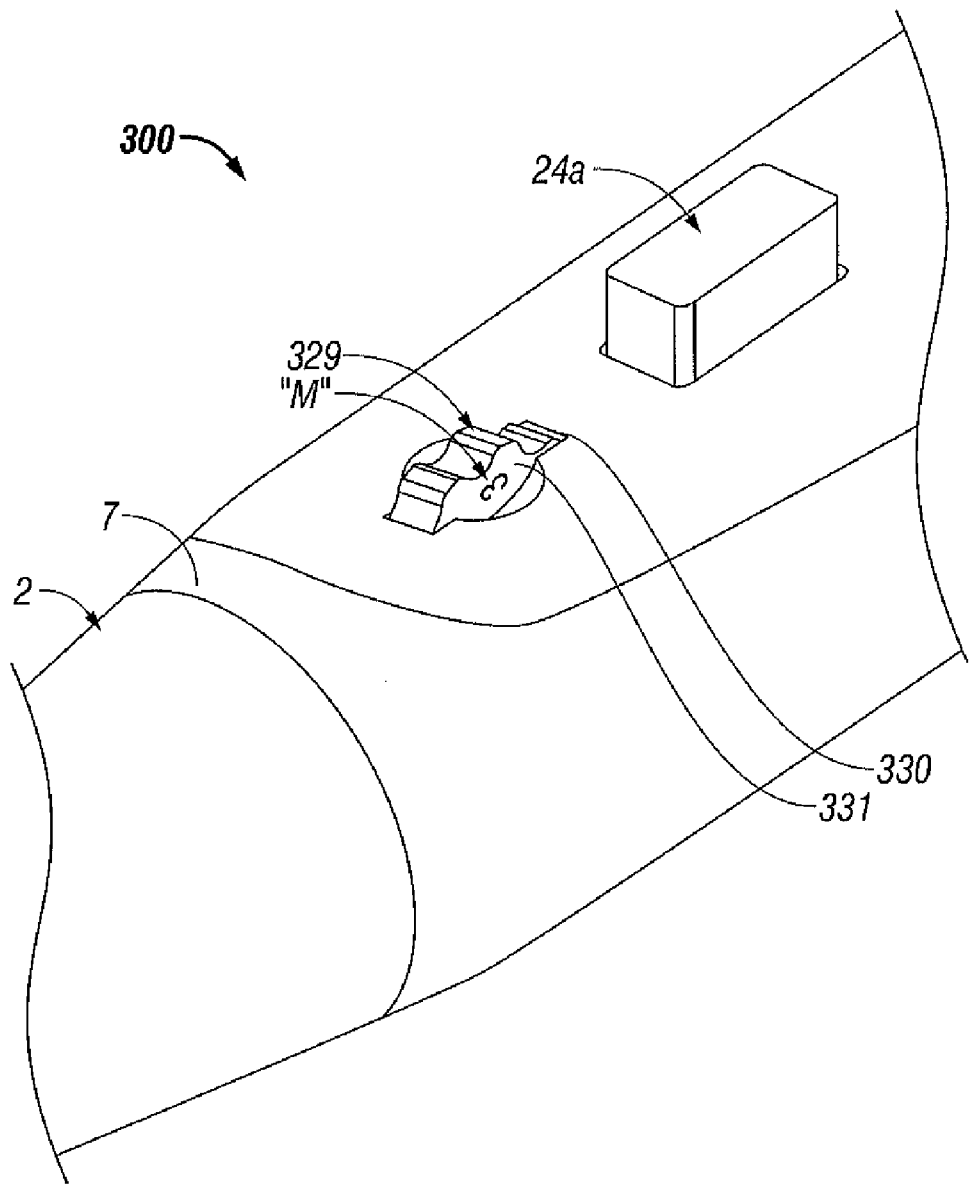
FIG. 9 is an enlarged perspective view of a portion of an electrosurgical pencil illustrating a set of exemplary switches disposed thereon.
Figure 10:
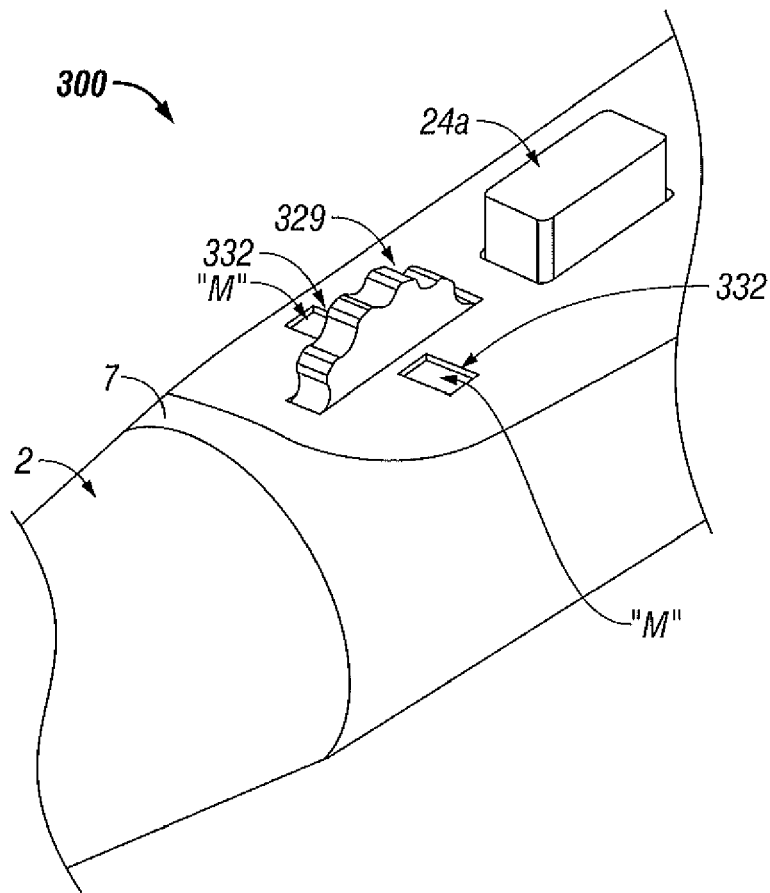
FIG. 10 is an enlarged perspective view of a portion of an electrosurgical pencil illustrating another set of exemplary switches disposed thereon.
Figure 11:
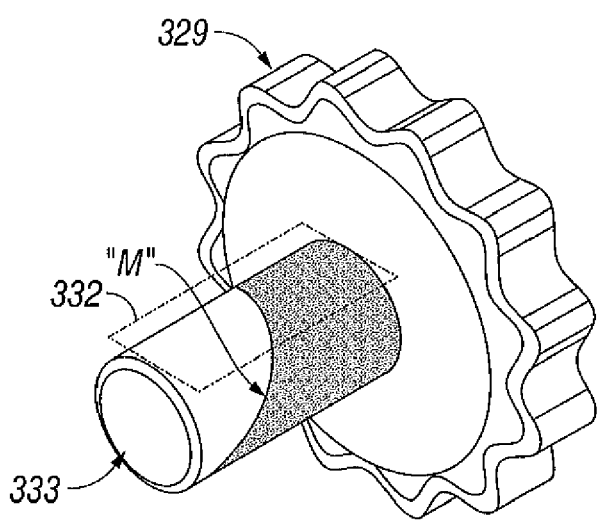
FIG. 11 is a perspective view of the switch of FIG. 10.

Turning now to FIGS. 9-11, an electrosurgical pencil, in accordance with still another embodiment of the present disclosure, is generally designated as 300. Electrosurgical pencil 300 is similar to electrosurgical pencil 10 and/or 100 and will only be discussed in detail to the extent necessary to identify differences in construction and operation. As seen in FIGS. 9 and 10, nubs 29a, 29b have been replaced with a dial 329 rotatably supported in an aperture 330 formed in outer surface 7 of housing 2. In embodiments, dial 329 may be positioned forward of activation switch 24a such that dial 329 is not inadvertently rotated during the depression of any one of activation switches 24a-24c. Further, dial 329 may be configured and adapted to adjust the power parameters or, alternatively, the frequency parameters to adjust the perceived output intensity and perceived output frequency, respectively.

As seen in FIG. 9, a side surface 331 of dial 329 can be provided with indicia and/or markings "M" in the form of a scale and/or other form of gradient to indicate to the surgeon the degree of and/or level of power/frequency at which electrosurgical pencil 300 is set.

As seen in FIGS. 10 and 11, windows 332 can be formed on either side of dial 329 in outer surface 7 of housing 2. As seen in FIG. 11, windows 332 provide the surgeon with visibility to indicia "M" provided on stub 333 extending from the central axis of dial 329. Indicia "M" can be in the form of numbers, letters, colors and, as seen in FIGS. 10 and 11, an enlarging gradient. In embodiments, each dial 329 may perform a dual function, for example, dial 329 can be rotated to set the desired power/frequency level and can be pressed down to activate the electrosurgical pencil with the desired mode.

In embodiments, electrosurgical pencil 100 may include a smart recognition technology that communicates with the generator to identify the electrosurgical pencil and communicate various surgical parameters that relate to treating tissue with electrosurgical pencil 100. For example, the electrosurgical pencil 100 may be equipped with a bar code or Aztec code that is readable by the generator and presets the generator to default parameters associated with treating tissue with electrosurgical pencils. The bar code or Aztec code may also include programmable data that is readable by the generator and programs the generator to specific electrical parameters prior to use.

Other smart recognition technology may be included that enables the generator to determine the type of instrument being utilized or to insure proper attachment of the instrument to the generator as a safety mechanism. One such safety connector is identified in U.S. Pat. No. 7,131,860, the entire contents of which are incorporated herein by reference. For example, in addition to the smart recognition technology described above, such a safety connector can include a plug or male portion operatively associated with the electrosurgical pencil and a complementary socket or female portion operatively associated with the electrosurgical generator. Socket portion is "backward compatible" to receive connector portions of electrosurgical pencils disclosed therein and to receive connector portions of prior electrosurgical instruments.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An electrosurgical pencil, comprising:
an elongated housing;
an electrocautery electrode supported within the housing and extending distally from the housing, the electrocautery electrode configured to connect to a source of electrosurgical energy; and
at least one voltage divider network supported on the housing, the at least one voltage divider network electrically connected to the source of electrosurgical energy and configured to transmit at least one characteristic signal to the source of electrosurgical energy for controlling at least one of a frequency, an intensity, and a mode of electrosurgical energy delivered by the source of electrosurgical energy to the electrocautery electrode, the at least one voltage divider network configured to control the frequency of the electrosurgical energy separately from the mode of the electrosurgical energy.

2. The electro surgical pencil according to claim 1, further including a plurality of activation switches supported on the housing, each activation switch configured to activate a particular mode of electrosurgical energy produced by the source of electrosurgical energy.

3. The electrosurgical pencil according to claim 2, wherein the at least one voltage divider network includes at least one slide potentiometer operatively supported on the housing.

4. The electrosurgical pencil according to claim 3, wherein the at least one slide potentiometer is configured to vary the frequency of electrosurgical energy delivered to the electrocautery electrode from a minimum of about 470 kHz to a maximum of about 1 MHz.

5. The electrosurgical pencil according to claim 4, wherein the at least one slide potentiometer is configured to adjust the frequency of a waveform duty cycle corresponding to a particular mode of the electrosurgical energy.

6. The electrosurgical pencil according to claim 5, wherein the at least one slide potentiometer is configured to provide a plurality of discreet frequency settings.

7. The electrosurgical pencil according to claim 5, wherein the at least one slide potentiometer has a first position corresponding to a minimum frequency, a second position corresponding to a maximum frequency and a plurality of positions between the first and second positions corresponding to frequencies between the minimum and the maximum frequency.

8. The electrosurgical pencil according to claim 4, wherein the at least one slide potentiometer is configured to selectively actuate the at least one voltage divider network to transmit the at least one characteristic signal to the source of electrosurgical energy for varying the frequency of electrosurgical energy delivered to the electrocautery electrode.

9. The electrosurgical pencil according to claim 4, wherein the at least one slide potentiometer is configured to selectively actuate the at least one voltage divider network to transmit the at least one characteristic signal to the source of electrosurgical energy for varying the frequency of a waveform duty cycle corresponding to a particular mode of the electrosurgical energy.

10. The electrosurgical pencil according to claim 3, wherein the at least one slide potentiometer is configured to control at least one of the intensity and the frequency of electrosurgical energy delivered to the electrocautery electrode.

11. The electrosurgical pencil according to claim 10, wherein the at least one slide potentiometer comprises at least one nub extending from a surface thereof, wherein the at least one nub is configured to contact the at least one voltage divider network and adjust the at least one characteristic signal transmitted by the at least one voltage divider network as the at least one slide potentiometer is moved relative to the housing.

12. The electrosurgical pencil according to claim 3, wherein the plurality of activation switches are configured to selectively actuate a first resistor network of the at least one voltage divider network, and wherein the at least one slide potentiometer is configured to selectively actuate at least one of a second resistor network and a third resistor network of the at least one voltage divider network.

13. The electrosurgical pencil according to claim 3, wherein the at least one slide potentiometer is set to a minimum when the at least one slide potentiometer is placed at a first position and is set to a maximum when the at least one slide potentiometer is placed at a second position.

14. The electrosurgical pencil according to claim 3, wherein the at least one slide potentiometer includes a pair of nubs slidably supported, one each, on either side of the plurality of activation switches such that the at least one slide potentiometer is operable from either side of the electrosurgical pencil.

15. The electrosurgical pencil according to claim 3, wherein the at least one slide potentiometer is configured to selectively actuate the at least one voltage divider network to transmit the at least one characteristic signal to the source of electrosurgical energy for controlling the at least one of the intensity and the frequency of electro surgical energy delivered to the electrocautery electrode.

16. The electrosurgical pencil according to claim 1, wherein the at least one voltage divider network is rotatably supported on the housing.

17. The electrosurgical pencil according to claim 1, wherein the at least one voltage divider network is configured to provide analog frequency settings.

18. The electro surgical pencil according to claim 1, wherein the plurality of activation switches are configured to selectively actuate the at least one voltage divider network to transmit the at least one characteristic signal to the source of electrosurgical energy for controlling the mode of electrosurgical energy delivered to the elecrocautery electrode.

19. An electrosurgical pencil, comprising:
an elongated housing;

an electrocautery electrode supported within the housing and extending distally from the housing, the electrocautery electrode operable to connect to a source of electrosurgical energy;

at least one voltage divider network supported on the housing, the at least one voltage divider network operable to electrically connect to the source of electrosurgical energy and configured to transmit at least one characteristic signal to the source of electrosurgical energy for controlling at least one of a frequency, a duty cycle, and an intensity of electrosurgical energy delivered to the electrocautery electrode by the source of electrosurgical energy; and a frequency controller slidably supported on the housing and configured to selectively actuate the at least one voltage divider network to transmit the at least one characteristic signal to the source of electrosurgical energy for controlling the frequency of the electrosurgical energy produced by the source of electrosurgical energy separately from the duty cycle.

20. The electrosurgical pencil according to claim 19, further comprising a plurality of activation switches supported on the housing and configured for selective engagement with the at least one voltage divider network, each activation switch configured to selectively complete a control loop extending from the source of electrosurgical energy to the at least one voltage divider network upon actuation thereof.

21. The electrosurgical pencil according to claim 20, wherein the plurality of activation switches define a first resistor network disposed within the housing, and wherein the frequency controller defines a second resistor network disposed within the housing.

22. The electrosurgical pencil according to claim 19, further comprising an intensity controller slidably supported on the housing, wherein the intensity controller is configured to selectively actuate the at least one voltage divider network and provide a tactile feedback to a user of the electrosurgical pencil as the intensity controller is moved relative to the housing.

23. The electrosurgical pencil according to claim 22, wherein the intensity controller is configured to selectively actuate the at least one voltage divider network to transmit the at least one characteristic signal to the source of electrosurgical energy for controlling the intensity of the electrosurgical energy produced by the source of electrosurgical energy.

24. The electrosurgical pencil according to claim 19, wherein the frequency controller selectively actuates the at least one voltage divider network to transmit the at least one characteristic signal to the source of electrosurgical energy which in turn transmits a corresponding waveform frequency to the electrocautery electrode.

25. The electrosurgical pencil according to claim 19, wherein the frequency controller has a first position corresponding to a minimum frequency of the electrosurgical energy, a second position corresponding to a maximum frequency of the electrosurgical energy and a plurality of positions between the first and second positions corresponding to frequencies between the minimum and the maximum frequency of the electrosurgical energy.

26. An electrosurgical pencil, comprising:
an elongated housing;
an electrocautery electrode supported within the housing and extending distally from the housing, the electrocautery electrode configured to connect to a source of electrosurgical energy;

at least one voltage divider network supported on the housing, the at least one voltage divider network electrically connected to the source of electrosurgical energy and configured to transmit at least one characteristic signal to the source of electrosurgical energy for controlling at least one of a frequency, an intensity, and a mode of electrosurgical energy delivered to the electrocautery electrode by the source of electrosurgical energy, the voltage divider network configured to control the frequency of the electrosurgical energy separately from the mode of the electrosurgical energy;

a frequency controller slidably supported on the housing and configured to selectively actuate the at least one voltage divider network to transmit the at least one characteristic signal to the source of electrosurgical energy for controlling the frequency of the electrosurgical energy;

an intensity controller slidably supported on the housing and configured to selectively actuate the at least one voltage divider network to transmit the at least one characteristic signal to the source of electrosurgical energy for controlling the intensity of the electrosurgical energy separately from the mode of the electrosurgical energy; and a plurality of activation switches supported on the housing, the plurality of activation switches configured to selectively actuate the at least one voltage divider network to transmit the at least one characteristic signal to the source of electrosurgical energy for controlling the mode of electrosurgical energy, each activation switch corresponding to a particular mode of electrosurgical energy produced by the source of electrosurgical energy.

27. An electrosurgical pencil, comprising:
an elongated housing;
an electrocautery electrode supported within the housing and extending distally from the housing, the electrocautery electrode configured to connect to a source of electrosurgical energy; and a voltage divider network supported by the housing and electrically connected to the source of electrosurgical energy, the voltage divider network configured to transmit at least one characteristic signal to the source of electrosurgical energy upon actuation thereof for controlling electrosurgical energy delivered to the electrocautery electrode by the source of electrosurgical energy;

at least one duty cycle controller supported on the housing and operably coupled to the voltage divider network, the at least one duty cycle controller configured to actuate the voltage divider network to select a duty cycle of the electrosurgical energy delivered to the electrocautery electrode; and a frequency controller supported on the housing and operably coupled to the voltage divider network, the frequency controller configured to actuate the voltage divider network to adjust the frequency of the electrosurgical energy delivered to the electrocautery electrode for each selected duty cycle.

* * * * *